United States Patent
Angele et al.

(10) Patent No.: US 6,737,072 B1
(45) Date of Patent: May 18, 2004

(54) MATRIX FOR TISSUE ENGINEERING FORMED OF A HYALURONIC ACID ESTER AND HYDROLYZED COLLAGEN

(75) Inventors: Peter Angele, Regensburg (DE); Richard Kujat, Pettendorf (DE)

(73) Assignee: Michael Nerlich, Pentling (DE)

( * ) Notice: Subject to any disclaimer, the term of this patent is extended or adjusted under 35 U.S.C. 154(b) by 0 days.

(21) Appl. No.: 09/857,343

(22) PCT Filed: Dec. 3, 1999

(86) PCT No.: PCT/EP99/09444

§ 371 (c)(1),
(2), (4) Date: Sep. 4, 2001

(87) PCT Pub. No.: WO00/32251

PCT Pub. Date: Jun. 8, 2000

(30) Foreign Application Priority Data

Dec. 3, 1998 (DE) .......................................... 198 55 890

(51) Int. Cl.⁷ ........................... C61F 2/00; C12N 11/02; C12N 5/06; C12N 5/08
(52) U.S. Cl. ...................... 424/426; 424/93.7; 435/177; 435/395
(58) Field of Search ................................ 435/177, 325, 435/395; 424/423, 93.7, 426

(56) References Cited

U.S. PATENT DOCUMENTS

| | | | | |
|---|---|---|---|---|
| 5,834,232 A | * | 11/1998 | Bishop et al. | 435/68.1 |
| 5,866,165 A | * | 2/1999 | Liu et al. | 424/486 |
| 5,939,323 A | * | 8/1999 | Valentini et al. | 435/395 |
| 6,423,347 B1 | * | 7/2002 | Aoyagi et al. | 424/570 |

FOREIGN PATENT DOCUMENTS

| | | |
|---|---|---|
| EP | 0648480 A2 | 4/1995 |
| WO | WO 97/18842 | 5/1997 |
| WO | WO 97/45532 | 12/1997 |
| WO | WO 98/31345 | 7/1998 |

* cited by examiner

Primary Examiner—David M. Naff
(74) Attorney, Agent, or Firm—Heller Ehrman White and McAuliffe (57) ABSTRACT

A porous composite matrix is formed from a hyaluronic acid derivative and hydrolyzed collagen, which are preferably in a weight ratio range of 30:70 to 99:1. A preferred hyaluronic acid derivative is an ester such as an ethyl or benzyl ester. The matrix is prepared by dissolving the hyaluronic acid derivative and hydrolyzed collagen in a first solvent, adding a pulverulent compound virtually insoluble in the first solvent, removing the first solvent, and dissolving the pulverulent compound in a second solvent. The matrix is used as a biocompatible and biodegradble composite matrix for the tissue engineering of chondral and osseous tissue and for the repair of muscoskeletal defects.

23 Claims, 4 Drawing Sheets

MATRIX FOR TISSUE ENGINEERING FORMED OF A HYALURONIC ACID ESTER AND HYDROLYZED COLLAGEN

BACKGROUND OF THE INVENTION

1. Field of the Invention

The invention relates to a porous, composite matrix formed from a hyaluronic acid derivative and hydrolyzed collagen, which is used as a biocompatible and biodegradable composite matrix for the repair of muculoskeletal defects.

2. Description of the Related Art

For the regeneration of tissue defects, it is necessary to use a body-compatible, slowly biodegradable matrix which under suitable conditions makes possible the differentiation of introduced cells with marked production of a specific intercellular matrix. Various matrices of this type are known in the prior art.

WO 97/28192 discloses a process for the preparation of prion-free collagen products which can be used as a spongy implant. For ocular applications, the collagen product can be crosslinked with 5% by weight hyaluronic acid to increase the transparency. The hyaluronic acid additionally stimulates the cell infiltration into the implant.

WO 91/18553 and WO 91/16857 and also U.S. Pat. No. 4,830,429 disclose composite matrices formed from collagen and up to 25% by weight of glycosaminoglycans such as hyaluronic acid.

EP-A-0 784 985 discloses a porous composite article which comprises a bioabsorbable hydrophilic material selected from gelatin, hyaluronic acid and a hyaluronic acid derivative. To avoid premature absorption, the article is additionally provided with a polymer layer which is absorbed in a delayed manner.

WO 97/14376 discloses a bone transplant matrix formed from collagen, which can contain hyaluronic acid as a birding agent.

U.S. Pat No. 5,676,964 discloses inter- and intramolecularly crosslinked esters of acidic polysaccharides such as God preferably hyaluronic acid. These esters can be employed as biodegradable, for example spongy, materials as surgical articles.

The known matrices, however, show marked restrictions in the provision of suitable medium conditions for the differentiation of introduced cells (e.g. premature absorption, unsuitable matrix composition) and are also unsatisfactory with respect to the stability necessary or handling.

SUMMARY OF THE INVENTION

An object of the present invention thus consists in making available a matrix which assists cell differentiation and intercellular matrix production and is then itself slowly degraded. Moreover, the matrix should have an adequate stability which makes the matrix highly suitable and easy to handle not only for preculture of cells in vitro but also for in-vivo implantation.

It has now been found that this object is achieved bag a composite matrix formed from a hyaluronic acid derivative and hydrolyzed collagen of specific composition.

The present invention thus relates to a porous composite matrix, the matrix being synthesized on matrix formers comprising a hyaluronic acid derivative and a hydrolyzed collagen, and the matrix formers being present in a weight ratio range of hyaluronic acid derivative to hydrolyzed collagen of 30:70 to 99:1.

DETAILED DESCRIPTION OF THE INVENTION

As matrix former, the composite matrix according to the invention comprises a hyaluronic acid derivative and hydrolyzed collagen, preferably in a weight ratio of 60:40 to 99:1 and particularly preferably of approximately 70:30.

Preferably, the matrix is synthesized only from the hyaluronic acid derivative and the hydrolyzed collagen.

It has been shown that matrices having a proportion of hyaluronic acid derivative of below 30% bow ;eight are technically disadvantageous on account of too low a stability. Conversely, it was possible by means of the composite matrix according to the invention comprising a hyaluronic acid derivative and hydrolyzed collagen markedly to improve cell adhesion, matrix loading with cells and subsequent cell differentiation compared with matrices comprising 100% hyaluronic acid derivative, such as are known, for example, from U.S. Pat. No. 5,676,964 mentioned at the outset.

Moreover, a component which can be degraded in a delayed manner is absorbed directly into the composite matrix by the hyaluronic acid derivative. By means of this, for example, the additional coating disclosed in EP-A-0 784 985 can be avoided, or a collagen derivatization which may otherwise be necessary, which is undesirable on account of the toxicity of the derivatizing agent which has been detected in some cases.

A suitable hydrolyzed collagen is partially and/or completely hydrolyzed collagen, in particular gelatin, i.e. collagen in highly hydrolyzed form. For example, gelatin from pigs or cattle can be employed. However, forms of gelatin having a higher aggregation rate along the lines of fibrils can also be employed. More highly aggregated collagen can lead to an improvement in matrix stability. Those collagens having degradation forms of different size can be produced by a controlled, slow hydrolysis of fibrillar collagen.

If desired, the hydrolyzed collagen can additionally be derivatized and/or crosslinked.

As a hyaluronic acid derivative for the preparation of the composite matrix according to the invention, hyaluronic acid esters such as ethyl esters and in particular benzyl esters are preferred on account of their better biomechanical properties, it being possible for the hyaluronic acid tow have different degrees of esterification. Examples of hyaluronic acid esters which can be employed according to the invention are mentioned in U.S. Pat. No. 5,676,964. The disclosure of this U.S. patent is thus incorporated into the present description.

Advantageously, the hyaluronic acid derivative employed is predominantly hydrophobic.

A preferred hyaluronic acid ester is a benzyl ester of hyaluronic acid (HYAFF), which can be ordered, for example, from "Fidia Advanced Biopolymers" from Abano Therme in Italy. HYAFF is supplied in various degrees of esterification, of which a highly esterified benzyl hyaluronate "HYAFF 11" (100% benzyl ester), which is commercially obtainable as the already licensed wound dressing material "JALOSKIN", is preferred according to the invention.

Other hyaluronic acid esters having lower degrees of esterification (for example HYAFF 11 p 75, a benzyl hyaluronate having a degree of esterification of about 75%) and/or other alcohol radicals, such as ethyl hyaluronate (for example HYAFF 7), or with mixtures of various alcohol radicals, however, can also be employed.

The composite matrix according to the invention is porous, in particular open-pore. Preferably, the pores in the composite matrix have an average diameter in the range of 10–1000 µm, in particular 50–500 µm. It has been shown that excessively large pores (>1000 µm) lead on population with cells to a high cell loss from the matrix, particularly with small sponge diameters. With excessively small pores (>100 µm), a strong sieve effect is seen and the cells cannot be populated in deeper regions of the matrix. However, a lower density and a looser structure of the composite matrix can be achieved by means of a specific proportion of smaller pores. By this means, an acceleration of the degradation in vivo can be achieved without alteration of the pore size accessible to the cells.

Pores having an average diameter in the range of 100–350 µm and pores having an average diameter in the range of 350–1000 µm have proven advantageous. If a lower density or a looser structure of the composite matrix is desired, pores in the range of 10–100 µm, in particular in the range of approximately 50 µm, can additionally be present. Pores of approximately equal size or pores having a size gradient can also be made available.

The composite matrix according to the invention can additionally be chemically or physically crosslinked. By this means, the biodegradability of the composite matrix can be delayed if required. Moreover, premature leaching of possible additives can be prevented. A suitable crosslinking agent is, for example, cyanamide, which crosslinks proteins and polysaccharides and on biological degradation produces no exogenous, harmful residues, as it is degraded to urea.

The composite matrix according to the invention can moreover comprise biologically active compounds. These can be, for example, compounds which optimize the property of the matrix of populating cells, for example antibiotics, compounds for improving cell adhesion, calcium salts, inductive factors or further glycosaminoglycans and their derivatives. Advantageously, cell adhesion can be improved by addition of highly polymeric poly-L-lysine or coating with an activated succinyl derivative of poly-L-lysine or the admixture of fibronectin or peptides having RGD sequences.

In order to optimize the use of the composite matrix according to the invention in the therapy of osseous tissue defects, the matrix can contain calcium salts such as, for example, calcium sulfates, calcium phosphates and calcium carbonates, for example as suspension or solution.

To decrease the risk of infection on the implantation of the composite matrix according to the invention, said matrix can also contain antibiotics.

As further biologically active compounds, the composite matrix according to the invention can contain, for example, inductive factors for optimizing the repair of musculoskeletal defects, in particular cytokines such as bFGF (fibroblast growth factor), IGF (insulin-like) growth factor) or TGFbeta (transforming growth factor)

The composite matrix is particularly suitable for the in-vitro and in-vivo generation of differentiated tissue from chondrocytic cells, mesenchymal stem and progenitor cells, osteoblasts and connective tissue cells. The invention thus also relates to composite matrices which comprise these cells.

A further aspect of the present invention is a process for the production of the porous composite matrix described above. This process comprises dissolving or suspending the hyaluronic acid derivative and the hydrolyzed collagen in a suitable first solvent, the addition of a pulverulent compound which is virtually insoluble in the first solvent, but which is soluble in a second solvent, in which the matrix formers hyaluronic acid derivative and hydrolyzed collagen are virtually insoluble, to the solution or suspension, the pulverulent compound having an average particle size distribution in the range of the desired pore size of the composite matrix to be produced, the removal of the first solvent and subsequently the dissolution of the pulverulent compound in a second solvent, in which the pulverulent compound dissolves and the matrix formers are virtually insoluble.

A suitable first solvent is, in particular, 1,1,1,3,3,3-hexafluoroisopropanol (HFIP). This is a highly volatile liquid in which esterified hyaluronic acid, hydrolyzed collagen (gelatin) and further substances necessary for the specific requirements, such as growth factors and calcium compounds, can be simultaneously dissolved or suspended at room temperature. The larger the molecular units of the hydrolyzed collagen, the poorer their solubility in HFIP. Fibrillar collagen is no longer dissolved.

The concentrations of the starting substances in the first solvent are insignificant for the process according to the invention and can be varied as long as handleable solutions or suspensions are obtained. This relates both to the concentrations of the individual components, and the total concentration of the components in the first solvent. The individual concentrations of the hyaluronic acid derivative and the hydrolyzed collagen determine the weight ratio of the two components in the final product. Finally, as the first solvent is stripped off the final product, the total concentration determines the density and solidity of the final product.

For the handling of the composite matrix according to the invention, its mechanical strength in the wet state plays an important role. The solidity of the composite matrix is greatest if there is a high hyaluronic acid derivative content in the matrix, as the matrix swells the least here. With growing content of the hydrolyzed collagen, the composite matrix swells increasingly strongly and becomes less stable.

Preferably, 5% by weight HYAFF is dissolved in HFIP in the process according to the invention. For this, gelatin can be admixed in a variable individual concentration of, for example, up to 7.5% by weight, such that a high total concentration of 12.5% by weight of matrix former is achieved in the solution. On account of this, the decrease in the solidity is compensated because of the strong swelling. Solutions having a total concentration of more than 12.5% by weight are very viscous and are difficult to handle. An increase in the content of gelatin in the final product can therefore only be carried out if the HYAFF content is reduced. However, a reduction in the HYAFF content (for example to an individual concentration of 2.77% by weight with a total concentration of 9.23% by weight of the matrix former in the solution, which corresponds to a weight ratio of HYAFF to gelatin of 30:70) decreases the stability of the matrix without producing an improvement in the biocompatibility.

In principle, the addition of gelatin has a positive effect on the biocompatibility and on the histogenic property of the matrix. A weight ratio of hyaluronic acid derivative to hydrolyzed collagen of approximately 70:30 proved suitable in vitro and in vivo, but, depending on the application, for example for the formation of cartilage or for the regeneration of bone tissue, optimum weight ratios can be in the range from 99:1 to 60:40.

Pore formation is carried out by addition of a pulverulent compound which is virtually insoluble in the first solvent. If HFIP is used as the first solvent, sodium chloride, for example, is suitable as a pulverulent compound for pore formation. Sodium chloride is virtually insoluble in HFIP, moreover it is nontoxic and cheap.

In addition to sodium chloride, any alkali metal or alkalino earth metal salt, in particular halide, which is water-soluble and insoluble in HFIP is suitable as the first solvent when using HFIP. For the reasons mentioned above, however, sodium chloride is preferred.

The amount of the pulverulent compound added determines the pore number and thus the density and also solidity of the matrix produced. The weight ratio of solution or suspension to sodium chloride crystals of approximately 1:2 has proven to be advantageous.

The pore size is determined by the selection of the particle size of the pulverulent compound. Commercially available sodium chloride mainly has particles having a diameter of between 500 and 1000 $\mu$m. Fractions of smaller size can easily be produced by grinding larger grains in a mortar and by screening through calibrated screens.

The mixture of HYAFF, gelatin and sodium chloride crystals has the consistency of a thick paste. By pressing with a die in molds, for example of inert plastic (PTFE, PE, PVC), it is possible to produce matrix objects whose shape can largely be adapted to requirements. As HFIP is very volatile as a solvent, rapid drying of the mixture takes place. Because of this, the mixture should be stored in closed vessels and processed as quickly as possible. Drying can take place, for example, overnight under a hood and subsequently for a few hours in vacuo. The composite matrix can then be removed from the mold.

As the mixture scarcely shrinks during drying, releasing the matrix can cause difficulties. Because of this, the molds should be designed such that the dried contents can be forced out with a ram. For example, cylindrical matrices having a diameter of 3–18 mm and a height of 2–15 mm can easily be produced. For the production of larger matrix blocks, cuboid, trough-shaped molds which are put together from dismantleable wall and bottom parts have proven particularly suitable.

The pores of the composite matrix according to the invention are then obtained by dissolving the pulverulent compound in a second solvent in which the pulverulent compound dissolves and the matrix formers are virtually insoluble. If sodium chloride crystals are used as pulverulent compound, a suitable second solvent is in particular water. Repeated rinsing in pure water removes the salt and possibly still adherent traces of HFIP. In the case of small samples, four changes of the second solvent are recommended after an immersion time of 15 minutes in each case, with larger samples 6 changes after 20 minutes in each case.

On the first drying of the composite matrix by evaporating the first solvent, closed pores having grains of salt contained therein are primarily produced. During the washing process, the semi-permeable substance of the matrix swells and the formation of an osmotically highly active salt solution occurs in the pores. As a result of this, on further absorption of water the pores burst and the matrix finally becomes open-pore.

If desired, the composite matrix can additionally be loaded with biologically active compounds as mentioned above by way of example during or after production. Advantageously, the biologically active compounds are added to the solution or suspension of the matrix components even before the addition of the pulverulent compound.

The composite matrix thus produced is advantageously then dried. This can be achieved, for example, by immersion in acetone of increasing concentration (50%, 80%, 100%), blotting on filter paper and subsequent drying in vacuo.

Finally, it is advisable to remove a thin surface layer of the composite matrix, for example using a sharp blade, as a high number of closed pores remains in this layer, which prevents the deep penetration of cells.

Before loading with cells, the composite matrix is advantageously sterilized. This can be carried out by various known sterilization processes such as with alcohol, ethylene oxide or by gamma sterilization. A gamma sterilization with, for example, 350,000 rad is preferred.

The composite matrix according to the invention is suitable for the in-vitro and in-vivo generation of differentiated tissue from chondrocytic cells, mesenchymal stem and progenitor cells, osteoblasts and connective tissue cells. On account of a specifically adapted matrix composition and matrix geometry, the repair of musculoskeletal defects is hereby possible.

The present invention thus also relates to the use of the composite matrix described above for the generation of differentiated tissue from chondrocytic cells or mesenchymal stem and progenitor cells, in which freshly removed or amplified cells are added to the composite matrix and optionally cultured under chondro-, osteor- or fibrogenic conditions.

By addition of freshly removed chondrocytes or mesenchymal stem and progenitor cells or of dedifferentiated chondrocytes or mesenchyaml stem and progenitor cells which are amplified in vitro to the composite matrix according to the invention under chondrogenic culture conditions, a biomechanically loadable joint cartilage tissue can thus be prepared. The composite matrix according to the invention is thus suitable for the tissue engineering of tissue types of the connective and supportive apparatus, in particular of chondral and osseous tissue.

A biocompatible and biodegradable composite matrix produced in this way is thus suitable without or with prior in-vitro culturing for in-vivo differentiation to give tissue types of the connective and supportive apparatus, in particular to give chondral and osseous tissue under ectopic or autotopic implantation.

The composite matrix according to the invention is suitable, for example, for human chondrocytes which have been obtained from hyaline cartilage. Hyaline joint cartilage from autopsies and residual cartilage supplies from the carrying-out of total endoprostheses can be the origin of removal here. Embryonic chondrocytes, such as can be obtained, for example, from abortions are additionally suitable. Moreover, adult mesenchymal stem and progenitor cells, for example from bone marrow, synovium or periostium and preferably embryonic mesenchymal stem and progenitor cells, for example from the umbilical cord, can be used. Embryonic mesenchymal stem cells offer the advantage of a lack of rejection in allogenic transplantation. Moreover, they are constantly available in adequate number and can be obtained without an additional intervention on the patient.

A further aspect of the present invention is an implant which comprises a porous composite matrix according to the invention. Such an implant, which is preferably coated with the composite matrix, has the advantage that better integration in the bone and optionally also the surrounding connective tissue is produced.

Suitable implant surfaces which are coated with the composite matrix according to the invention are, in particular, metal surfaces, such as titanium or steel, a polymer or ceramics.

The composite matrix according to the invention has the advantage that, on loading the matrix with cells, only a small change in size occurs. On loading with cells, known collagen matrices show great differences in size (initially massive swelling, then a strong tendency to form into a ball). For use of tissue engineering (in-vitro production of tissue with the aim of incorporating this into a defect), however, size stability of the matrix is also of great importance after cell loading and culturing. This is achieved by the composite matrix according to the invention and in particular by the simultaneous mixing of the matrix formers using HFIP.

Moreover, the following further advantages are achieved using the composite matrix according to the invention:

In stationary culture, a redifferentiation of amplified chondrocytes in the composite matrix is possible. Cartilage-typical proteoglycans (chondroitin sulfate, keratan sulfate, aggregan) and collagen II are formed. It was possible to detect these after culturing for 2, 4 and 6 weeks.

The product produced in vitro from chondrocytes cultured on the composite matrix shows a marked increase in biomechanical stability in comparison to the starting condition at the point in time of the application of cells to the matrix.

Without cells, the matrix dissolves in vitro after about 14 days. In vivo, resorption can be observed after about 6–8 weeks (nude mice, rabbits).

Good differentiation ability of bone marrow cells to hyaline-like tissue in vitro.

Very good differentiation to give osseous tissue on incorporation into subcutaneous tissue of nude mice, resorption of the matrix in vivo only after 6 weeks.

On incorporation into osteochondral defects in the knee joint of rabbits, integration of the cell matrix construct is recognizable (cells were in this case bone marrow cells or chondrocytes), differentiation to cartilaginous tissue is recognizable. In the osseous defect portion, bone integration and differentiation to give new bone tissue is seen.

No proneness to inflammation by material in the knee joint detectable (no hydrarthrosis, no massive increase in inflammatory cells). Incorporation of the cell matrix construct into meniscus defects of rabbits after prior culturing in vitro possible, good regeneration of the meniscus defect, no proneness to inflammation in the knee joint.

In combination with the hyaluronic acid derivative, the adverse swelling in the case of gelatin or collagen otherwise occurring after moistening of the dry matrix is not produced. This is particularly favorable for tissue engineering matrices, in which a certain prespecified defect area is to be repaired.

Figure 1A:
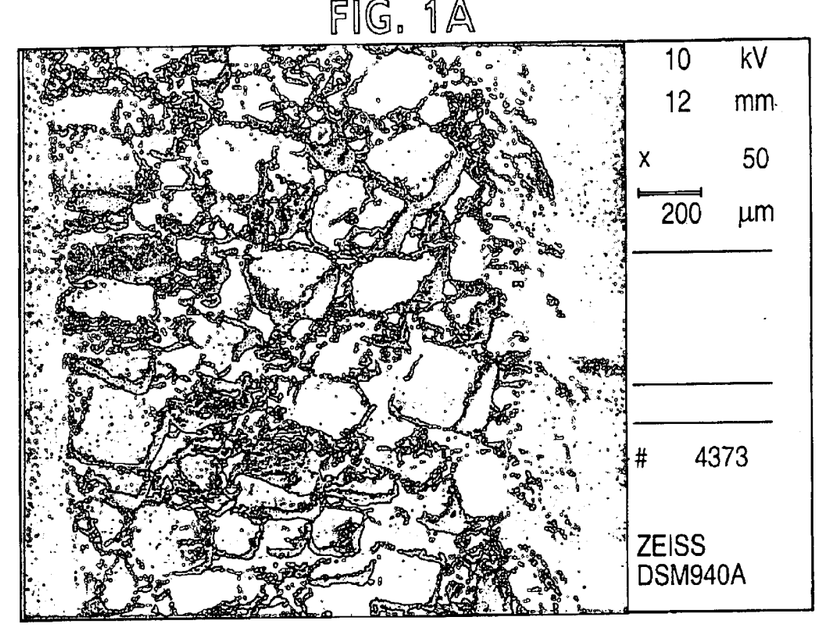
FIGS. 1A and 1B show a 50 times magnification of a more stable structure A and a weaker structure B.
Figure 1B:
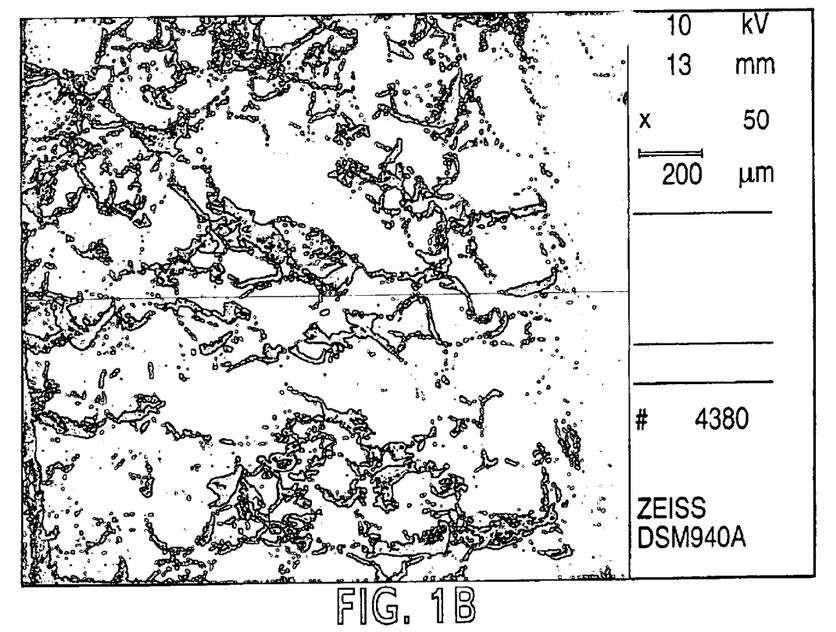
Figure 2A:
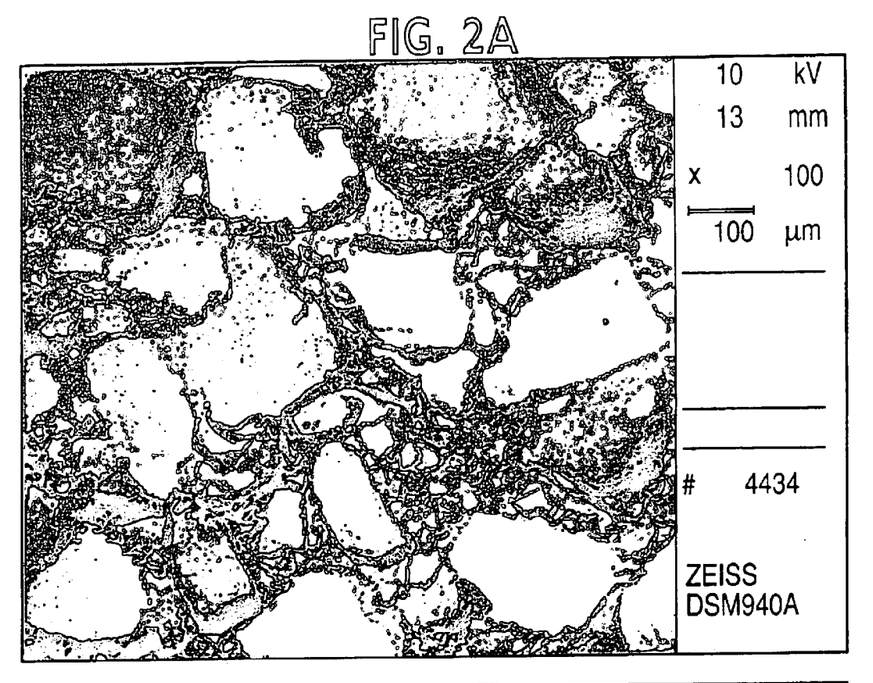
FIGS. 2A and 2B show a 100 times magnification of the more stable structure A and the weaker structure B.
Figure 2B:
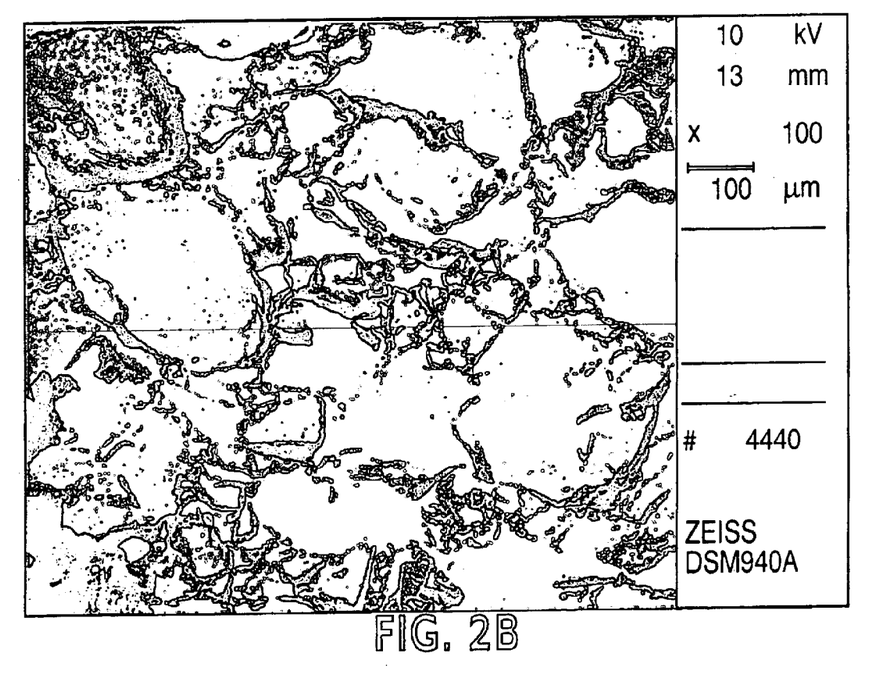
Figure 3A:
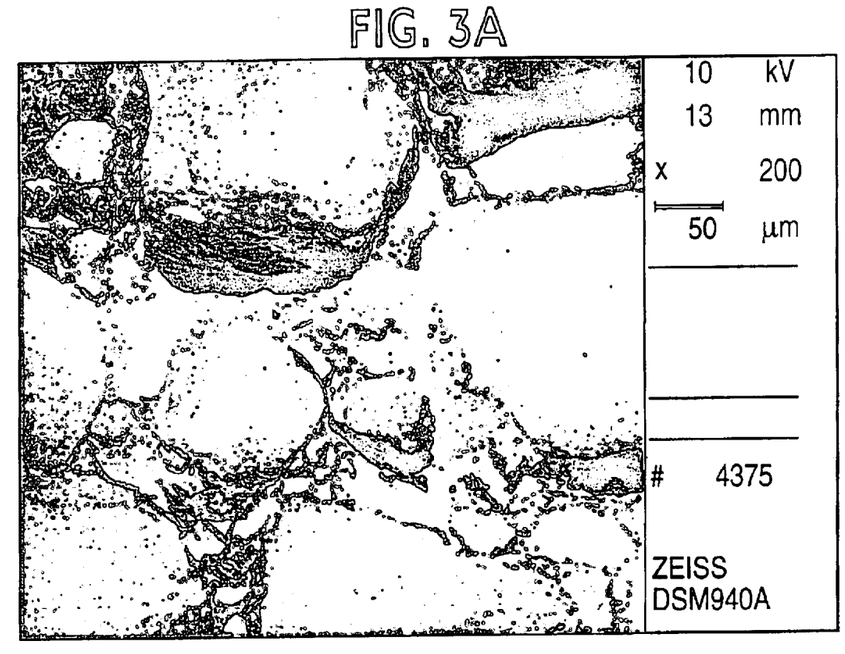
FIGS. 3A and 3B show a 200 times magnification of the more stable structure A and the weaker structure B and FIGS. 4A and 4B show chondrocytes growing in the pores under 200 times magnification A and 1000 times magnification B.
Figure 3B:
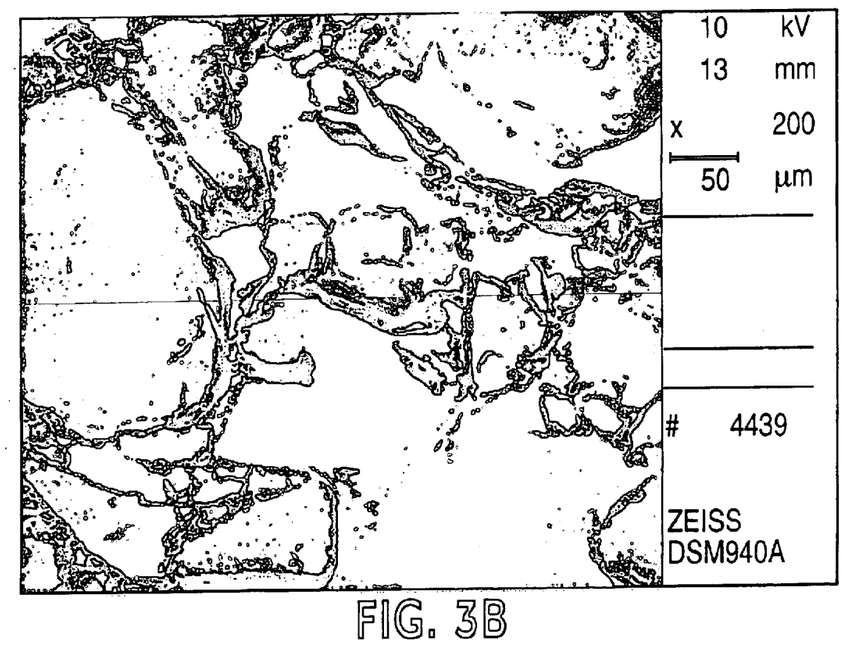

The attached figures show magnifications of the composite matrix according to the invention:

The more stable structure in each case in FIGS. 1–3 was obtained by means of a higher total concentration of the matrix components in the solution during production, the total concentration being varied from 6.3% for the weaker structure to 9.2% for the more stable structure.

Figure 4A:
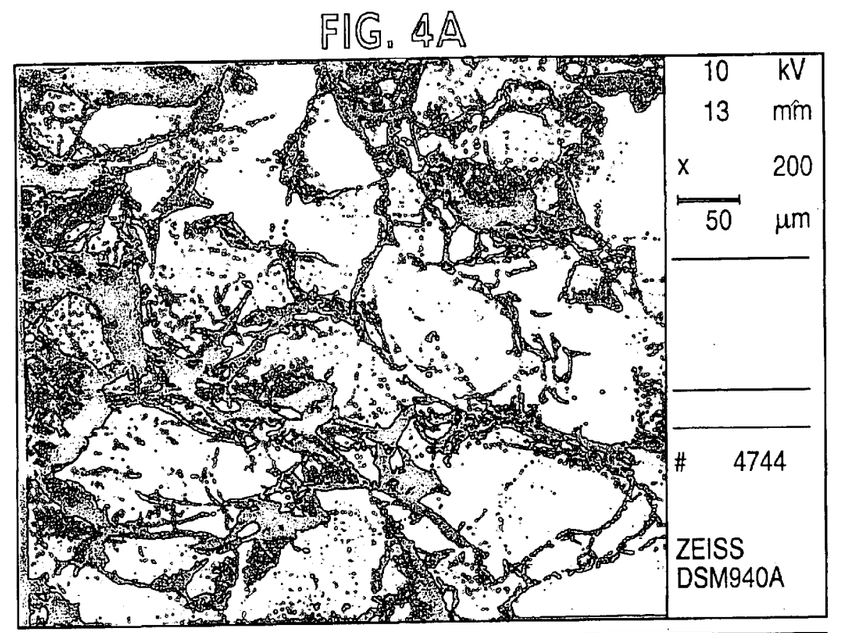
Figure 4B:
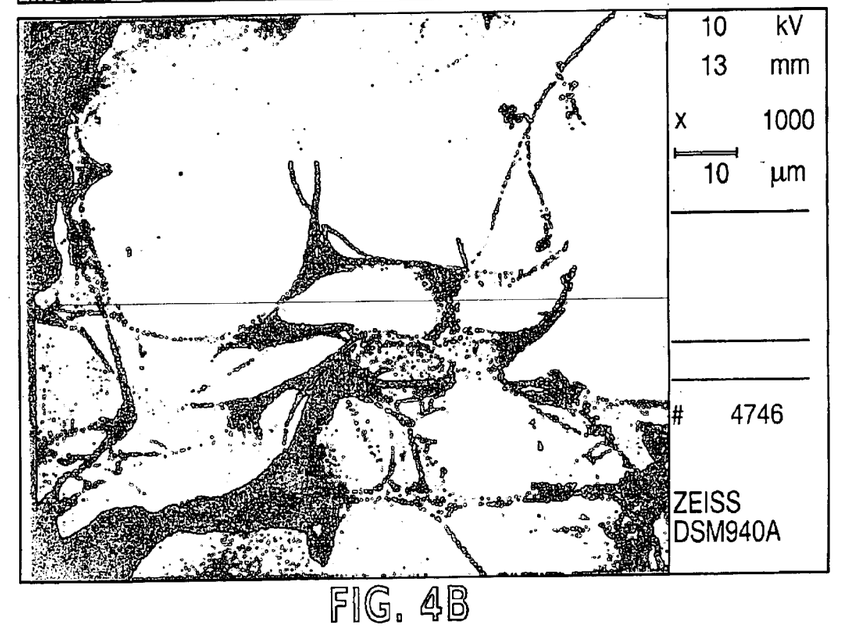

The threadlike structures in FIG. 4 indicate the beginning of production of the extracellular matrix.

The following examples are intended to explain the present invention in greater detail.

EXAMPLE 1

A composite matrix according to the invention was produced by dissolution of HYAFF and gelatin in HFIP, addition of sodium chloride crystals, shaping and drying of the resulting paste, and by removal of the sodium chloride by repeated rinsing with water. After drying, the composite matrix was subjected to gamma sterilization.

EXAMPLE 2

Description of Production

Obtainment of Chondrocytes for the Primary Cell Culture
Adult Joint Cartilage/Embryonic Cartilage After removal, hyaline joint cartilage (adult/embryonic) was immediately transferred to RPMI medium and worked up as rapidly as possible (less than 24 h). For this, the cartilage was first separated mechanically from the bone and then comminuted using a scalpel (final size: pieces of cartilage 1–2 mm in size). Enzymatic partial digestion with collagenase, hyaluronidase and DNAse was then carried out at 37° C. with continuous swirling. The enzymes were resuspended in RPMI medium with HEPES buffer, L-glutamine and addition of penicillin/streptomycin (antibiotic addition). The optimized enzymatic dissociation interval was 12 hours. The enzymatic activity was buffered by addition of serum-containing medium (RPMI with 10% AB serum or RPMI with 10% fetal bovine serum (FBS). Pieces of extracellular matrix still remaining were then extracted by filtering and centrifuging the suspension, discarding the supernatant and resuspending the cell pellet in RPMI containing 10% AB serum or RPMI containing 10% FBS. After cell counting, stationary culturing and amplification of the chondrocytes for 14–21 days (2 times per week change of medium with serum-containing medium). After reaching confluence, the cells were passaged (removal of the medium, addition of 0.25% trypsin, after abolishment of cell adherence addition of serum-containing medium, centrifugation of the cell suspension and resuspension of the pellet then obtained in fresh medium, cell counting and renewed sowing of the cells) . A 1 in 4 division was usually carried out here, i.e. one culture bottle yielded the cells for 4 new bottles. After renewed confluence (about 2–4 weeks), the cells (secondary culture) were detached from the culture bottom by renewed trypsin treatment (see above) and prepared for the treatment of the matrices.

It is also possible, however, to use cells in primary and tertiary culture (2 passaging steps).

Embryonic Mesenchymal Stem and Progenitor Cells From the Umbilical Cord

The cells were cultured in DMEM medium containing 10% FBS and, after reaching confluence, used as a primary culture for matrix loading. The adherent cells were again obtained by the application of trypsin described above.

Adult Mesenchymal Stem and Progenitor Cells From Bone Marrow

Bone marrow was obtained from the iliac crest of white New Zealand hares 4 months old. Dulbecco's Modified Eagle's Medium (DMEM) containing 10% fetal bovine serum (FBS) was added to the aspirate. After determination of the cell count, $20 \times 10^6$ cells were cultured at 37° C. with 5% $CO_2$ in 100 mm culture dishes. The medium was changed twice per week until the cells were 80% confluent. Adherent cells were treated with trypsin as described above, counted, washed and resuspended in DMEM to a final concentration of $5 \times 10^5$ cells/25 µl.

Matrix Treatment

For matrix treatment, the cell pellet was taken up in a little medium (1 mm³/1 µl). After this, the matrix (sterile, previously dry) was loaded from one side. The escape of air which was situated in the matrix was thereby ensured (time of action 1–5 minutes). After this, still remaining medium with a high cell concentration was transferred to the matrix by production of an under- and overpressure using a pipette tip. A distribution of cells in the matrix which is as homogeneous as possible should be achieved. The loading can be facilitated by the addition of detergents.

A 2 h incubation in an incubator (37° C., 5% $CO_2$) then followed. This allowed the cells to adhere to the matrix present.

Finally, the cell-matrix construct was completely coated with medium and cultured further.

Description of Culture

Stationary Culture

For this, different culture media were used:

RPMI containing 10% AB serum (human),

RPMI containing 10% FBS or

Dulbecco's Modified Eagle's Medium (DMEM) having a high glucose content and nutrients and additives (ITS and pyruvate plus dexamethasone, ascorbic acid and TGF betal). (Cf. B. Johnstone in Exp. Cell Res. 238 (1998)).

Continuous Perfusion Culture

An alternative culturing condition is the continuous profusion culture in RPMI medium containing 10% AB serum.

EXAMPLE 3

In order to investigate the efficiency of reloading of the composite matrix according to the invention with cells, a composite matrix produced according to Example 1 was loaded with the bone marrow cells obtained according to Example 2. Some of the matrices were immediately fixed in formalin, washed and embedded in paraffin (Group I). Other loaded matrices (Group II) were cultured for 14 days in a chondrogenic medium comprising DMEM with ITS+ premixture (Collaborative Biomechanical Products), pyruvate (1 mM), ascorbic acid 2-phosphate (37.5 µg/ml), dexamethasone ($10^{-7}$M) and TGF-β1 (10 ng/ml). The medium was changed three times weekly.

The cell suspension was introduced into the matrix with slight swelling of the construct. By means of Toluidine Blue-stained areas of the matrices from Group I, it was possible to show that a high cell loading was present in all pores of the matrices. After 14 days under chondrogenic culture conditions (Group II), the originally soft cell matrix constructs had hardened. The Toluidine Blue-stained areas showed cells having a marked metachromatically staining extracellular matrix, which was present in the entire composite matrix. The extracellular matrix contained collagen II.

EXAMPLE 4

Composite matrices loaded with cells as in Example 3 were implanted subcutaneously into immunodeficient mice (Group III). The same matrices were cultured for 14 days in vitro in the chondrogenic medium described in Example 3 and then implanted in vivo (Group IV). The implants were removed after 3 weeks, fixed in formalin, decalcified and embedded in paraffin.

5 µm thick disks of the samples were cut and stained using Toluidine Blue. The stained areas were assessed according to their osteochondral differentiation (0 (neither bone nor cartilage in the matrix pores) to 4 (more than 75% of the pores contain bone and/or cartilage)).

After 3 weeks in vivo, a significant size change occurred neither in the Group III nor in the Group IV implants. The implants precultured for 14 days in vitro (Group IV) appear, however, to be qualitatively harder than the composite matrices which were implanted immediately after loading with the cells (Group III). The staining with Toluidine Blue produced an osteochondral differentiation of cells in composite matrices of both groups, in which the pores filled with cartilage and bone. The composite matrices of Group IV, however, contained more bone and cartilage (average assessment=4, compared with an assessment of 3 for Group III). Additionally, the content of bone in the samples of Group IV was greater (ratio of bone: cartilage: fibrous tissue in Group III: 40:20:40 and in Group IV: 85:10:5).

What is claimed is:

1. A porous composite matrix, comprising a matrix constructed from matrix formers comprising a hyaluronic acid derivative and a hydrolyzed collagen, and wherein the matrix formers are present in a weight ratio range of hyaluronic acid derivative to hydrolyzed collagen of 30:70 to 99:1, and wherein the hyaluronic acid derivative is a hyaluronic acid ester.

2. The composite matrix as claimed in claim 1, wherein the matrix formers are present in a weight ratio range of hyaluronic acid derivative to hydrolyzed collagen of 60:40 to 99:1.

3. A composite matrix as claimed in claim 1, wherein the hydrolyzed collagen is partially or completely hydrolyzed.

4. A composite matrix as claimed in claim 1, wherein the hydrolyzed collagen is additionally derivatized and/or crosslinked.

5. A composite matrix as claimed in claim 1, wherein the hyaluronic acid ester is an ethyl or benzyl ester of hyaluronic acid.

6. A composite matrix as claimed in claim 1, further comprising pores having an average diameter in the range of 10–1000 µm.

7. A composite matrix as claimed in claim 6, wherein the pores have an average diameter in the range of 100–350 µm.

8. A composite matrix as claimed in claim 6, wherein the pores have an average diameter in the range of 350–1000 µm.

9. A composite matrix as claimed in claim 7 further comprising pores in the range of 10–100 µm.

10. A composite matrix as claimed in claim 1, further comprising crosslinkages.

11. A composite matrix as claimed in claim 1, further comprising biologically active compounds.

12. A composite matrix as claimed claim 1, further comprising chondrocytes, mesenchymal stem cells, mesenchymal progenitor cells, osteoblasts and connective tissue cells.

13. The composite matrix as claimed in claim 1, wherein the matrix formers are present in a weight ratio of hyaluronic acid derivative to hydrolyzed collagen of approximately 70:30.

14. A composite matrix as claimed in claim 8, further comprising pores in the range of 10–100 µm.

15. The composite as claimed in claim 11, wherein the biologically active compounds are selected from the group consisting of antibiotics, compounds for improving cell adhesion, calcium salts, inductive factors, glycosaminoglycans other than hyaluronic acid derivatives of the glycosaminoglycans other than hyaluronic acid.

16. An implant, comprising a porous composite matrix as claimed in claim 1.

17. A process for the production of the porous composite matrix of the implant as claimed in claim 16, comprising the steps of:
- dissolving or suspending the hyaluronic acid derivative and the hydrolyzed collagen in a first solvent;
- adding a pulverulent compound that is virtually insoluble in the first solvent, but which is soluble in a second solvent in which the hyaluronic acid derivative and hydrolyzed collagen are virtually insoluble;
- removing the first solvent; dissolving the pulverulent compound in the second solvent to obtain said porous composite matrix.

18. A process for generating differentiated tissue from chondrocytic cells or mesenchymal stem and progenitor cells, comprising adding freshly removed or amplified cells to a composite matrix as claimed in claim 1, and culturing said cells under chondro-, osteo-or fibrogenic conditions.

19. A process for generating differentiated tissue from chondrocytic cells or mesenchymal stem and progenitor cells, comprising culturing cells added to a composite matrix as claimed in claim 1 under chondro-, osteo-or fibrogenic conditions.

20. The process as claimed in claim 18, wherein said differentiated tissue is suitable for use as connective and supportive tissue.

21. The process as claimed in claim 18, wherein said tissue is differentiated in-vivo and is suitable for use as connective and supportive tissue.

22. The process as claimed in claim 20, wherein said tissue is chondral and osseous tissue.

23. The process as claimed in claim 21, wherein said tissue is chondral or osseous tissue.

* * * * *